United States Patent [19]

Van Berkel et al.

[11] 4,222,964

[45] Sep. 16, 1980

[54] 2-(2,2-DIHALOVINYL-3,3-DIMETHYLCYCLOPROPYL)ETHANAL

[75] Inventors: Johannes Van Berkel; Johannes L. M. Syrier; Hendrik C. Kelderman, all of Amsterdam, Netherlands

[73] Assignee: Shell Oil Company, Houston, Tex.

[21] Appl. No.: 55,855

[22] Filed: Jul. 9, 1979

[30] Foreign Application Priority Data

Jul. 19, 1978 [GB] United Kingdom ............... 30372/78

[51] Int. Cl.$^3$ ............................................. C07C 47/21
[52] U.S. Cl. .................................... 568/420; 568/591; 562/506; 560/231; 560/193
[58] Field of Search ......................................... 260/598

[56] References Cited

U.S. PATENT DOCUMENTS

| 2,676,988 | 4/1954 | Robeson et al. | 260/598 X |
|---|---|---|---|
| 2,676,992 | 4/1954 | Humphlett | 260/598 |
| 4,049,706 | 9/1977 | Dalton | 260/598 X |
| 4,085,148 | 4/1978 | Cleare | 260/601 H |

OTHER PUBLICATIONS

Methoden der Organischem Chemie, (Houber-Weyl), vol VII, Part 1, (1954), pp. 423-428 & 442-445.

*Primary Examiner*—Bernard Helfin

[57] ABSTRACT

2-(2,2-Dihalovinyl-3,3-dimethylcyclopropyl)ethanal is a new chemical compound and useful intermediate in the preparation of certain pyrethroid esters. It is prepared by hydrolysis of 2-[2-(2,2-dihalovinyl)-3,3-dimethylcyclopropyl]ethylidene diacetate, preferably in the presence of an acid.

3 Claims, No Drawings

2-(2,2-DIHALOVINYL-3,3-DIMETHYLCYCLO-PROPYL)ETHANAL

BACKGROUND OF THE INVENTION

Field of the Invention

The present invention is directed to novel 2-(2,2-dihalovinyl-3,3-dimethylcyclopropyl)ethanals, their preparation and their use as intermediates in the preparation of certain synthetic pyrethroids.

SUMMARY OF THE INVENTION

The present invention is directed to novel 2-(2,2-dihalovinyl-3,3-dimethylcyclopropyl)ethanals of the formula I

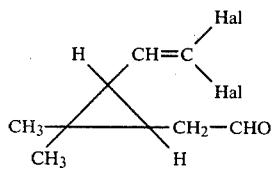

wherein each Hal independently represents a fluorine, chlorine or bromine atom.

These compounds have two asymmetric carbon atoms in the cyclopropane ring and, therefore, can have the (1R,cis), (1R,trans), (1S,cis) or (1S,trans) optical configuration. The nomenclature used herein to describe the spatial configurations has been defined by M. Elliott et al. in *Nature*, 248 (1974), pages 710–711. Among the four spatial configurations of these compounds, the (1R,cis) configuration is preferred, because the resulting pyrethroid esters usually have the highest pesticidal activity.

The above ethanals are useful intermediates for the preparation of dihalovinyl pyrethroids, such as those of the type described in U.S. Pat. No. 4,024,163. The ethanal is treated with an alkanoic acid anhydride, e.g., in the presence of an amine, to yield a 2-(2,2-dihalovinyl-3,3-dimethylcyclopropyl)vinyl alkanoate, which when ozonized followed by oxidative decomposition yields the desired free 2-(2,2-dihalovinyl)-3,3-dimethylcyclopropanecarboxylic acid, as described in the concurrently filed U.S. Pat. application Ser. No. 55,858.

The invention also provides a process for the preparation of the 2-(2,2-dihalovinyl-3,3-dimethylcyclopropyl)ethanals, which comprises hydrolyzing 2-[2-(2,2-dihalovinyl)-3,3-dimethylcyclopropyl]ethanal dimethyl acetals of the formula II

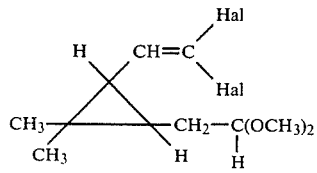

wherein each Hal has the meaning defined above in formula I. The hydrolysis is readily carried out in acidic medium. The hydrolysis of acetals is also described in, e.g., "Methoden der Organischen Chemie" (Houben-Weyl), Vol VII, Part 1, (1954), pages 423–8. When starting with the (1R,cis) isomer of compound II, the process according to the present invention affords the compound of formula I exclusively in the (1R,cis) configuration.

The ethanal dimethyl acetal starting materials II for this process originate from the natural terpene, carene. Carene is first ozonized and the resulting product treated with dimethyl sulfide in methanol to form 2-[2-(2-oxopropyl)-3,3-dimethylcyclopropyl]ethanal dimethyl acetate which is oxidized to the corresponding 2-methyl acetate. Hydrolysis of the acetate yields 2-(2-hydroxymethyl-3,3-dimethylcyclopropyl)ethanal dimethyl acetal. These steps are described in copending U.S. Pat. application Ser. No. 953,987, filed Oct. 23, 1978. Treatment of the 2-hydroxymethyl compound with a reactant capable of converting that group to a formyl group, e.g., pyridinium chlorochromate, yields 2-(2,2-dimethoxyethyl)-3,3-dimethylcyclopropanecarbaldehyde. When this carbaldehyde is added to the product of the reaction of a tri(dialkylamino)phosphine or an alkyl ester of an ortho-phosphorous acid bis(dialkylamide) with a compound generating a dihalocarbene yields the 2-(2,2-dihalovinyl)-3,3-dimethylcyclopropyl)ethanal starting material for the present process. These reactions are described in concurrently filed U.S. Pat. application Ser. No, 55,857.

The invention further provides a process for the preparation of the 2-(2,2-dihalovinyl-3,3-dimethylcyclopropyl)ethanals, which comprises hydrolyzing a 2-(2,2-dihalovinyl-3,3-dimethylcyclopropyl)ethylidene diacetate of formula III

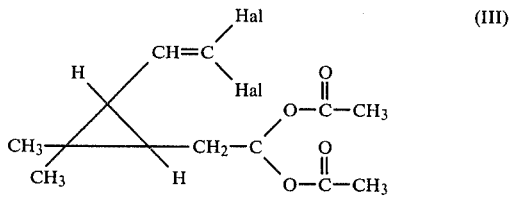

wherein each Hal has the meaning defined above in formula I. The hydrolysis is suitably carried out in the presence of an acid, for example, acetic acid to which a catalytic amount of sulfuric acid has been added. The hydrolysis of esters is described in, e.g., "Methoden der Organischen Chemie" (Houben-Weyl), Vol VII, Part 1 (1954), pages 442–5. When starting with the (1R,cis) isomer of compound III, the process according to the present invention affords the compound of formula I exclusively in the (1R,cis) configuration.

The ethylidene diacetate starting materials for this process originate from 4-hydroxy-2-carene. Initially this starting material is ozonized followed by reduction of the resulting product, both in the presence of an alkanol, to yield 4-acetyl-2-alkoxy-7,7-dimethyl-3-oxabicyclo[4.1.0]heptanes. The 2-methoxy compound is the preferred pyrethroid intermediate and is hydrolyzed with aqueous acid to yield 2-(2-hydroxy-3-oxobutyl)-3,3-dimethylcyclopropanecarbaldehyde which is readily converted to 1-(2-formyl-3,3-dimethylcyclopropyl)-3-oxo-2-butyl acetate by treatment with, e.g., acetyl halide. This acetate is then added to the product of the reaction of a tri(dialkylamino)phosphine or an alkyl ester of an ortho phosphorous acid bis(dialkylamide) with a compound generating a dihalocarbene to yield 1-[2-(2,2-dihalovinyl)-3,3-dimethylcyclopropyl]-3-oxo-2-butyl acetate. Oxidation of this compound, e.g., with peroxy acid, yields 2-[2,2-dihalovinyl)-3,3-dimethylcyclopropyl]ethylidene diacetate. These reactions are described in the concurrently filed U.S. Pat. application Ser. No. 55,854.

ILLUSTRATIVE EMBODIMENTS

The following embodiments are provided to illustrate the present invention and should not be regarded as limiting the invention in any way. Yields and purities were determined by means of gas-liquid chromatography and nuclear magnetic resonance (NMR) spectroscopy. The NMR data quoted were recorded at 90 MHz using solutions of the compounds in deuterochloroform; the absorptions given are relative to a tetramethylsilane standard.

EMBODIMENT I (1R,cis)-2-[2-(2,2-dichlorovinyl)-3,3-dimethylcyclopropyl]-ethanal dimethyl acetal Tri(dimethylamino)phosphine (168.3 mmol) was added over a period of 12 minutes to a stirred solution of carbon tetrachloride (167.4 mmol) in pentane (360 ml) kept at 0° C. under nitrogen in a 1-1 flask. Then, the mixture in the flask was stirred for 30 minutes at 0° C. This finished the first step.

At 0° C. (1R,cis)-2-(2,2-dimethoxyethyl)-3,3-dimethylcyclopropanecarbaldehyde (66.4 mmol) was added dropwise to the suspension in the flask over a period of nine minutes. The temperature was increased to 12° C. over a period of 15 minutes and stirring was continued at the temperature for a further 15 minutes. This finished the second step. Then water (75 ml) was added at 12° C. and -13 after removal of the aqueous phase — the organic phase was washed with two 35ml portions of water. The washed organic phase was dried over anhydrous magnesium sulphate and the solvent was evaporated from the dried solution to give a residue (17.4 g) containing the desired product (100% (1R,cis), purity 88%, yield 91.1%).

The NMR spectrum of the desired product showed the following absorptions:

$\delta = 1.00$ ppm singlet $H_3C$—C—$CH_3$
$\delta = 3.33$ ppm singlet C—(O—$CH_3$)$_2$
$\delta = 5.59$ ppm doublet C=CH
$\delta = 1.13$ ppm singlet $\underline{H_3C}$—C—$CH_3$
$\delta = 4.33$ ppm triplet ($H_3C$—O)$_2$—C$\underline{H}$—
multiplets for the two H atoms bound to the ring and for HC—C$\underline{H_2}$—CH.

EMBODIMENT II (1R,cis)-2-(2,2-dichlorovinyl-3,3-dimethylcyclopropyl)ethanal

A 250 ml flask was charged with the residue (17.4 g, containing 60.5 mmol of (1R,cis)-2-[2-(2,2-dichlorovinyl)-3,3-dimethylcyclopropyl]ethanal dimethyl acetal obtained as described in Embodiment I above) and a 2/1 (v/v) mixture (90 ml) of acetic acid and water to which concentrated aqueous hydrochloric acid (0.02 ml, sp.gr. 1.19) had been added. The mixture in the flask was heated with stirring under nitrogen for two hours at 60° C. Then, most of the acetic acid and water was distilled off from the reaction mixture (60° C./13.3 kPa), the residue obtained was taken up in diethyl ether (100 ml), water (25 ml) was added to the ethereal solution and the pH of the liquid was increased to 7 by addition of sodium hydrogen carbonate. The neutralized liquid was washed with 20 ml portions of water, the washed liquid was dried over anhydrous magnesium sulphate and the diethyl ether was distilled off from the dried liquid to give a residue (13.8 g) containing the desired product (100% (1R,cis), purity 82.1%, yield 90.4%). The NMR spectrum of this product showed the following absorptions:

$\delta = 1.02$ ppm singlet $H_3C$—C—$CH_3$
$\delta = 2.43$ ppm double doublet $\underline{H_2}C$—C(O)H
$\delta = 9.81$ ppm triplet —C(O)$\underline{H}$
$\delta = 1.21$ ppm singlet $\underline{H_3C}$—C—$CH_3$
$\delta = 5.57$ ppm doublet Cl$_2$C=C$\underline{H}$
multiplets for the two H atoms bound to the ring.

EMBODIMENT III (1R,cis)-4-acetyl-2-methoxy-7,7-dimethyl-3-oxabicyclo[4.1.0]heptane A 250-ml round-bottomed flask was charged with (1R,cis)-4-hydroxy-2-carene (77 mmol), (1R,cis)-4-hydroxy-7,7-dimethyl-3-methylenebicyclo[4.1.0]heptane (55 mmol) and water-free methanol (50 ml). A mixture consisting of ozone and oxygen was passed through the liquid in the flask at a rate of 20 mmol of ozone per hour, while the temperature was maintained at 0° C. After 7.5 hours, no (1R,cis)-4-hydroxy-2-carene and (1R,cis)-4-hydroxy-7,7-dimethyl-3-methylenebicyclo[4.1.0]heptane could be detected in the flask. The reaction mixture was allowed to adopt a temperature of 20° C. and dimethyl sulphide (145 mmol) was added. The mixture was allowed to stand overnight at 20° C., the solvent was evaporated and the residue formed taken up in n-hexane (50 ml). The solution obtained was washed with two 25-ml portions of water and the washed solution was dried over anhydrous sodium sulphate. Evaporation of the solvent from the dried solution afforded a residue (22.85 g) which according to gas chromatography analysis consisted of 4-acetyl-2-methoxy-7,7-dimethyl-3-oxabicyclo[4.1.0]heptane (100% (1R,cis), yield 96%, based on the starting amount of 4-hydroxy-2-carene) and 4-hydroxy-7,7-dimethylbicyclo[4.1.0]-3-heptanone (100% (1R,cis), yield 97%, based on the starting amount of 4-hydroxy-7,7-dimethyl-3-methylenebicyclo[4.1.0]heptane). The residue was separated into its components by chromatography on basic alumina. 4-acetyl-2-methoxy-7,7-dimethyl-3-oxabicyclo[4.1.0]heptane was eluted with n-hexane and 4-hydroxy-7,7-dimethylbicyclo[4.1.0]-3-heptanone with diethyl ether. The Nuclear Magnetic Resonance spectrum of 4-acetyl-2-methoxy-7,7-dimethyl-3-oxabicyclo[4.1.0]heptane showed the following absorptions (using a solution of the compound in carbon tetrachloride and relative to a tetramethylsilane standard):

$\delta = 1.03$ ppm singlet, intensity 3, C$\underline{H_3}$—C—$CH_3$
$\delta = 1.08$ ppm singlet, intensity 3, $CH_3$—C—C$\underline{H_3}$
$\delta = 1.30 - 0.45$ ppm multiplet, intensity 2, two H atoms bound to the cyclopropane ring.
$\delta = 1.42$ ppm multiplet, intensity 1, CHC$\underline{H_2}$CH
$\delta = 1.95$ ppm multiplet, intensity 1, CHC$\underline{H_2}$CH
$\delta = 2.09$ ppm singlet, intensity 3, C(O)C$\underline{H_3}$
$\delta = 3.30$ ppm singlet, intensity 3, OC$\underline{H_3}$
$\delta = 3.78$ ppm two doublets, intensity 1, J=12 and 4 c/sec, OC$\underline{H}$—C(O)
$\delta = 4.70$ ppm singlet, intensity 1, H$_3$COC$\underline{H}$ The 4-acetyl-2-methoxy-7,7-dimethyl-3-oxabicyclo[4.1.0]heptane had a purity of 98% and showed an $[\alpha]_D^{24} = 47.72$ (Concentration 0.2 g/nl in benzene).

EMBODIMENT IV (1R,cis)-2-(2-hydroxy-3-oxabutyl)-3,3-dimethylcyclopropanecarbaldehyde A 50 ml flask was charged with 4-acetyl-2-methoxy-7,7-dimethyl-3-oxabicyclo[4.1.0]heptane prepared as in Embodiment III above (21.7 mmol, 100% (1R,cis)) and a 1:1 (v) mixture (10 ml) of acetic acid and water. After stirring of the contents of the flask for five hours at 20° C., water (30 ml) was added and the resulting mixture was extracted with two 25-ml portions of dichloromethane. The combined extract phases were washed with two 25-ml portions of a saturated aqueous solution of sodium hydrogen carbonate and then with a 10 %w aqueous solution (25 ml) of sodium chloride. The washed organic phase was dried over anhydrous magnesium sulphate and the solvent was evaporated from the dried organic phase at 1.3 kPa to leave a residue (3.5 g) containing 2-(2-hydroxy-3-oxobutyl)-3,3-dimethylcyclopropanecarbaldehyde (100% (1R,cis), yield 88%). The nuclear magnetic resonance spectrum of this desired product showed the following absorptions (using a solution of this product in deuterochloroform and relative to a tetramethylsilane standard):

$\delta = 1.24$ ppm singlet $\underline{H}_3C$—C—$CH_3$
$\delta = 2.22$ ppm singlet $\underline{H}_3C$—C=O
$\delta = 4.23$ ppm double of doublets $\underline{H}C$—OH
$\delta = 1.33$ ppm singlet $H_3C$—C—$C\underline{H}_3$
$\delta = 3.6$ ppm (variable) broad—$O\underline{H}$
$\delta = 9.69$ ppm doublet $\underline{H}$—C=O multiplets for each of the H atoms bound to the ring.

EMBODIMENT V (1R,cis)-1-(2-formyl-3,3-dimethylcyclopropyl)-3-oxo-2-butyl acetate Acetyl chloride (30 mmol) was added with stirring over a period of 30 minutes and at a temperature between 5 and 10° C. to a 50-ml flask charged with 2-(2-hydroxy-3-oxobutyl)-3,3-dimethylcyclopropanecarbaldehyde (19.0 mmol, 100% (1R,cis)), both spatial configurations around the C—OH present) prepared as in Embodiment IV above, pyridine (60 mmol) and dichloromethane (20 ml). Then, consecutively, stirring was continued for 15 minutes, the temperature was allowed to rise to 20° C., water (20 ml) was added, the resulting mixture was acidified with concentrated aqueous hydrochloric acid (s.g. 1.19) to pH of 2, the acidified mixture was allowed to split up by settling into an aqueous and an organic phase and after separating off the aqueous phase, the organic phase was washed with two 30-ml portions of a 10 %w aqueous solution of sodium chloride and a saturated aqueous solution (30 ml) of sodium hydrogen carbonate. The washed organic liquid was dried over anhydrous magnesium sulphate and the solvent was evaporated from the dried liquid at 1.3 kPa to leave a residue (3.3 g) containing 1-(2-formyl-3,3-dimethylcyclopropyl)-3-oxo-2-butyl acetate (100% (1R,cis), yield 77%). The nuclear magnetic resonance spectrum of this desired product showed the following absorptions (using a solution of this product in deuterochloroform and relative to a tetramethylsilane standard):

$\delta = 1.23$ ppm singlet $\underline{H}_3C$—C—$CH_3$
$\delta = 2.16$ ppm singlet $\underline{H}_3C$—C(O)—O—
$\delta = 5.07$ ppm doublet of doublets $H_2C$—$C\underline{H}$—O—
$\delta = 1.33$ ppm singlet $H_3C$—C—$C\underline{H}_3$
$\delta = 2.19$ ppm singlet $\underline{H}_3C$—C(O)—C
$\delta = 9.63$ ppm doublet $\underline{H}$—C=O multiplets for each of the H atoms bound to the ring and for HC—$C\underline{H}_2$—CH.

EMBODIMENT VI (1R,cis)-1-[2-(2,2-dichlorovinyl)-3,3-dimethylcyclopropyl]-3-oxo-2-butyl acetate Tri(dimethylamino)phosphine (40 mmol) was added at $-20°$ C. and with stirring under nitrogen to a 250-ml flask charged with carbon tetrachloride (40 mmol) and diethyl ether (160 ml). Then, the temperature was allowed to rise to $+10°$ C. This finished the first step. The resulting suspension was cooled to $-20°$ C. and a solution in diethyl ether (5 ml) of the (1R,cis) isomer of 1-(2-formyl-3,3dimethylcyclopropyl)-3-oxo-2-butyl acetate prepared as in Embodiment V above was added. Then, the temperature of the mixture was allowed to rise to 20° C. This finished the second step. Water (50 ml) was added, the mixture was stirred for 5 minutes and, after settling, the organic phase was isolated and washed with two 50-ml portions of water. The washed organic liquid was dried over anhydrous magnesium sulphate and the solvent was evaporated from the dried liquid at 1.3 kPa to leave a residue (3.5 g) containing 1-[2-(2,2-dichlorovinyl)-3,3-dimethylcyclopropyl]-3-oxo-2-butyl acetate (100% (1R,cis), yield 84%).

The NMR spectrum of this desired product showed the following absorptions:

$\delta = 1.04$ ppm singlet $\underline{H}_3C$—C—$CH_3$
$\delta = 2.19$ ppm singlet $\underline{H}_3C$—C(O)—C and $\underline{H}_3C$—C(O)—O—
$\delta = 5.05$ ppm doublet of doublets $H_2C$—$C\underline{H}$—O—
$\delta = 1.16$ ppm singlet $H_3C$—C—$C\underline{H}_3$
$\delta = 5.59$ ppm doublet $\underline{H}C$=$CCl_2$ multiplets for each of the H atoms bound to the ring and for HC—$C\underline{H}_2$—CH.

EMBODIMENT VII (1R,cis)-2-[2-(2,2-dichlorovinyl)-3,3-dimethylcyclopropyl]ethylidene diacetate The contents of a 50-ml flask charged with 1-[2-(2,2-dichlorovinyl)-3,3-dimethylcyclopropyl]-3-oxo-2-butyl acetate prepared as in Embodiment VI above (11.9 mmol, 100% (1R,cis) both spatial configurations around C—C(O)$CH_3$ present), chloroform (10 ml) and 3-chloroperbenzoic acid (26 mmol) were stirred magnetically for five hours at 20° C. Then, another quantity of 3-chloroperbenzoic acid (6 mmol) was added and stirring was continued for 16 hours. The reaction mixture obtained was mixed with dimethyl sulphide (2 ml), keeping the temperature at 20° C., stirring was continued for 15 minutes, dichloromethane (30 ml) was added, the suspended material was filtered off, the filtrate was washed with two 20-ml portions of a saturated aqueous solution of sodium hydrogen carbonate and two 20-ml portions of a 10%w aqueous solution of sodium chloride. The washed organic phase was dried over anhydrous magnesium sulphate and the solvent was evaporated (2 kPa) from the dried liquid to leave a residue (2.3 g) containing the desired (100% (1R,cis), yield 63%). The nuclear magnetic resonance spectrum of this product showed the following absorptions (using a solution of this product in deuterochloroform and relative to a tetramethylsilane standard):

$\delta = 1.05$ ppm singlet $\underline{H}_3C$—C—$CH_3$ $\delta = 1.15$ ppm singlet H$_3$C—C—CH$_3$
$\delta = 2.12$ ppm singlet both H$_3$C—C(O)—O—
$\delta = 5.62$ ppm doublet HC=CCl$_2$
$\delta = 6.86$ ppm triplet H—C—O—
multiplets for each of the H atoms bound to the ring and for HC—CH$_2$CH.

EMBODIMENT VIII (1R,cis)-2-(2,2-dichlorovinyl)-3,3-dimethylcyclopropyl)ethanal The contents of a 25 ml flask charged with residue obtained in Embodiment VII (0.85 g) containing 2.8 mmol of (1R,cis)-2-[2-(2,2-dichlorovinyl)-3,3-dimethylcyclopropyl]ethylidene diacetate, acetic acid (4 ml), water (4 ml) and concentrated sulphuric acid (s.g. 1.84, containing 1 mmol of H$_2$SO$_4$) were stirred magnetically during eight hours at 70° C. After cooling to 20° C., water (10 ml) was added, the mixture formed was extracted twice with dichloromethane (15 ml), the combined extracts were washed with two 20 ml-portions of a saturated aqueous solution (20 ml) of 10 %w sodium chloride. The washed solution was dried over anhydrous magnesium sulphate and the solvent was evaporated from the dried solution at 1.13 kPa to leave a residue (0.40 g) containing 2-(2,2-dichlorovinyl)-3,3-dimethylcyclopropyl)ethanal (100% (1R,cis), yield 70%).

We claim:

1. A 2-(2,2-dihalovinyl-3,3-dimethylcyclopropyl)ethanal wherein each halo independently is chloro, fluoro or bromo.

2. An ethanal according to claim 1 wherein each halo is chloro.

3. An ethanal according to claim 1 or 2 which is in the (1R,cis) isomer configuration.

* * * * *